(12) United States Patent
Lee et al.

(10) Patent No.: US 9,758,772 B2
(45) Date of Patent: Sep. 12, 2017

(54) L-THREONINE-PRODUCING MICROORGANISM AND PRODUCTION METHOD FOR L-THREONINE USING THE SAME

(71) Applicant: CJ Cheiljedang Corporation, Seoul (KR)

(72) Inventors: Ji Sun Lee, Incheon (KR); Kwang Ho Lee, Seoul (KR); Eun Sung Koh, Gyeonggi-do (KR); Hyung Joon Kim, Seoul (KR); Keun Cheol Lee, Gyeonggi-do (KR); Young Bin Hwang, Seoul (KR)

(73) Assignee: CJ Cheiljedang Corporation, Seoul (KR)

(*) Notice: Subject to any disclaimer, the term of this patent is extended or adjusted under 35 U.S.C. 154(b) by 47 days.

(21) Appl. No.: 14/899,676

(22) PCT Filed: Apr. 24, 2014

(86) PCT No.: PCT/KR2014/003613
§ 371 (c)(1),
(2) Date: May 13, 2016

(87) PCT Pub. No.: WO2014/208884
PCT Pub. Date: Dec. 31, 2014

(65) Prior Publication Data
US 2016/0281070 A1    Sep. 29, 2016

(30) Foreign Application Priority Data

Jun. 24, 2013  (KR) .................. 10-2013-0072181

(51) Int. Cl.
| | | |
|---|---|---|
| *C12P 13/08* | (2006.01) | |
| *C12P 13/02* | (2006.01) | |
| *C12N 9/10* | (2006.01) | |
| *C12N 1/20* | (2006.01) | |
| *C12P 21/06* | (2006.01) | |
| *C12P 19/34* | (2006.01) | |
| *C12N 15/00* | (2006.01) | |
| *C07H 21/04* | (2006.01) | |
| *C07K 1/00* | (2006.01) | |
| *C12N 9/12* | (2006.01) | |
| *C12N 15/70* | (2006.01) | |
| *C07K 14/245* | (2006.01) | |

(52) U.S. Cl.
CPC .......... *C12N 9/1247* (2013.01); *C07K 14/245* (2013.01); *C12N 15/70* (2013.01); *C12P 13/08* (2013.01); *C12Y 207/07006* (2013.01)

(58) Field of Classification Search
CPC ....... C12N 15/70; C12N 9/1247; C12P 13/08; C12Y 207/07006; C07K 14/245
USPC ......... 435/115, 129, 193, 252.33, 69.1, 91.1, 435/320.1; 536/23.1, 23.2; 530/350
See application file for complete search history.

(56) References Cited

U.S. PATENT DOCUMENTS

| | | | | |
|---|---|---|---|---|
| 5,175,107 A | * | 12/1992 | Debabov | ................ C12N 15/52 435/115 |
| 5,200,341 A | | 4/1993 | Obukowicz | |
| 6,156,532 A | | 12/2000 | Kimura et al. | |
| 6,338,956 B1 | * | 1/2002 | Kimura | ................... C12P 13/04 435/106 |
| 2007/0072194 A1 | | 3/2007 | Alper et al. | |

FOREIGN PATENT DOCUMENTS

| | | | | |
|---|---|---|---|---|
| CN | 102234668 A | | 11/2011 | |
| CN | 102234668 | * | 8/2012 | ............... C12N 1/20 |
| EP | 0 864 654 B1 | | 11/2001 | |
| JP | 2009-509533 A | | 3/2009 | |
| KR | 10-0576342-0000 B | | 4/2006 | |
| KR | 10-0608085 B1 | | 8/2006 | |
| KR | 10-1145943-0000 B | | 5/2012 | |
| KR | 10-2012-0083795 A | | 7/2012 | |
| KR | 10-2015-0035917 A | | 4/2015 | |
| WO | WO 96/26289 A | | 8/1996 | |
| WO | WO 2007/038564 | | 4/2007 | |
| WO | WO 2009/061429 | | 5/2009 | |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
International Search Report issued in PCT/KR2014/003613 dated Aug. 28, 2014.
Karlin S, Altschul SF, Proc Natl Acad Sci U S A. Jun. 15, 1993;90(12):5873-5877, "Applications and statistics for multiple high-scoring segments in molecular sequences".

(Continued)

*Primary Examiner* — Ganapathirama Raghu
(74) *Attorney, Agent, or Firm* — Swanson & Bratschun, L.L.C.

(57) ABSTRACT

The present application relates to an L-threonine-producing microorganism and a production method for L-threonine using the same, and more specifically, to a microorganism having enhanced L-threonine productivity and a method for producing L-threonine in high yield using the same.

9 Claims, No Drawings

(56) References Cited

OTHER PUBLICATIONS

Pearson W R, Methods Enzymol. 1990;183:63-98, "Rapid and sensitive sequence comparison with FASTP and FASTA" (abstract only).
Calendar et al. (Aug. 1988) Journal of Bacteriology, 170(8):3479-3484, "Deletion and Insertion Mutations in the rpoH Gene of *Escherichia coli* that Product Functional $\sigma^{32}$".
Grossman et al., Journal of Bacteriology, Mar. 1985, vol. 161, No. 3, pp. 939-943, "Mutations in the rpoH (htpR) Gene of *Escherichia coli* K-12 Phenotypically Suppress a Temperature-Sensitive Mutant Defective in the $\sigma^{70}$ Subunit of RNA Polymerase".
Obukowicz et al., Applied and Environmental Microbiology, May 1992, No. 5, pp. 1511-1523, "Enhanced Heterologous Gene Express in Novel rpoH Mutants of *Escherichia coli*".

\* cited by examiner ional Application No. PCT/KR2014/003613 filed on Apr. 24, 2014, and claims the benefit of Korean Application No. 10-2013-0072181, filed on Jun. 24, 2013, which is hereby incorporated by reference in its entirety for all purposes as if fully set forth herein

SEQUENCE LISTING

<160> NUMBER OF SEQ ID NOS: 17

<210> SEQ ID NO 1
<211> LENGTH: 35
<212> TYPE: DNA
<213> ORGANISM: Artificial Sequence
<220> FEATURE:
<223> OTHER INFORMATION: primer

<400> SEQUENCE: 1
cagtatccgg aattcgcttg cattgaactt gtgga                                35

<210> SEQ ID NO 2
<211> LENGTH: 35
<212> TYPE: DNA
<213> ORGANISM: Artificial Sequence
<220> FEATURE:
<223> OTHER INFORMATION: primer

<400> SEQUENCE: 2
gtcataccgg aattccttaa tagcggaaat tacgc                                35

<210> SEQ ID NO 3
<211> LENGTH: 35
<212> TYPE: DNA
<213> ORGANISM: Artificial Sequence
<220> FEATURE:
<223> OTHER INFORMATION: primer

<400> SEQUENCE: 3
cagtatccgg aattcgcttg cattgaactt gtgga                                35

<210> SEQ ID NO 4
<211> LENGTH: 35
<212> TYPE: DNA
<213> ORGANISM: Artificial Sequence
<220> FEATURE:
<223> OTHER INFORMATION: primer

<400> SEQUENCE: 4
gtcataccgg aattccttaa tagcggaaat tacgc                                35

<210> SEQ ID NO 5
<211> LENGTH: 27
<212> TYPE: DNA
<213> ORGANISM: Artificial Sequence
<220> FEATURE:
<223> OTHER INFORMATION: primer

<400> SEQUENCE: 5
atctagaaag cgcagcgcaa actgttc                                         27

<210> SEQ ID NO 6
<211> LENGTH: 50
<212> TYPE: DNA
<213> ORGANISM: Artificial Sequence
<220> FEATURE:
<223> OTHER INFORMATION: primer

<400> SEQUENCE: 6
ttcgtataat gtatgctata cgaacggtaa ccccggactc tcatccaggg               50

<210> SEQ ID NO 7
<211> LENGTH: 50
<212> TYPE: DNA
<213> ORGANISM: Artificial Sequence
<220> FEATURE:
<223> OTHER INFORMATION: primer

<400> SEQUENCE: 7
gcagagaacc ctggatgaga gtccggggtt accgttcgta tagcatacat               50

<210> SEQ ID NO 8
<211> LENGTH: 50
<212> TYPE: DNA
<213> ORGANISM: Artificial Sequence

```
<220> FEATURE:
<223> OTHER INFORMATION: primer

<400> SEQUENCE: 8
gtgattttat ccacaagttc aatgcaagcg gtacctaccg ttcgtataat                50

<210> SEQ ID NO 9
<211> LENGTH: 50
<212> TYPE: DNA
<213> ORGANISM: Artificial Sequence
<220> FEATURE:
<223> OTHER INFORMATION: primer

<400> SEQUENCE: 9
tagcatacat tatacgaacg gtaggtaccg cttgcattga acttgtggat                50

<210> SEQ ID NO 10
<211> LENGTH: 52
<212> TYPE: DNA
<213> ORGANISM: Artificial Sequence
<220> FEATURE:
<223> OTHER INFORMATION: primer

<400> SEQUENCE: 10
catccagggt tctctgctta atagcggaaa ttacgcttca atggcagcac gc             52

<210> SEQ ID NO 11
<211> LENGTH: 50
<212> TYPE: DNA
<213> ORGANISM: Artificial Sequence
<220> FEATURE:
<223> OTHER INFORMATION: primer

<400> SEQUENCE: 11
aaaaattgcg tgctgccatt gaagcgtaat ttccgctatt aagcagagaa                50

<210> SEQ ID NO 12
<211> LENGTH: 28
<212> TYPE: DNA
<213> ORGANISM: Artificial Sequence
<220> FEATURE:
<223> OTHER INFORMATION: primer

<400> SEQUENCE: 12
aaagctttgt ttcgggtcac aggcatcg                                        28

<210> SEQ ID NO 13
<211> LENGTH: 3136
<212> TYPE: DNA
<213> ORGANISM: Artificial Sequence
<220> FEATURE:
<223> OTHER INFORMATION: synthetic

<400> SEQUENCE: 13
aagcgcagcg caaactgttc ttcaacctgc gtaaaaccaa gcagcgtctg ggctggttta     60
accaggatga agtcgaaatg gtggcccgtg aactgggcgt aaccagcaaa gacgtacgtg    120
agatggaatc acgtatggcg gcacaggaca tgacctttga cctgtcttcc gacgacgatt    180
ccgacagcca gccgatggct ccggtgctct atctgcagga taaatcatct aacttttgccg   240 acggcattga agatgataac tgggaagagc aggcggcaaa ccgtctgacc gacgcgatgc    300
agggtctgga cgaacgcagc caggacatca tccgtgcgcg ctggctggac gaagacaaca    360
agtccacgtt gcaggaactg gctgaccgtt acggcgtttc cgctgagcgt gtacgccagc    420
```

```
tggaaaagaa cgcgatgaaa aaattgcgtg ctgccattga agcgtaattt ccgctattaa      480
gcagagaacc ctggatgaga gtccggggtt aggtgacact atagaacgcg gccgccagct      540
gaagctttac cgttcgtata gcatacatta tacgaagtta tctgccctga accgacgacc      600
gggtcgaatt tgctttcgaa tttctgccat tcatccgctt attatcactt attcaggcgt      660
agcaccaggc gtttaagggc accaataact gccttaaaaa aattacgccc cgccctgcca      720
ctcatcgcag tactgttgta attcattaag cattctgccg acatggaagc catcacagac      780
ggcatgatga acctgaatcg ccagcggcat cagcaccttg tcgccttgcg tataatattt      840
gcccatggtg aaaacggggg cgaagaagtt gtccatattg ccacgtttta aatcaaaact      900
ggtgaaactc acccagggat tggctgagac gaaaaacata ttctcaataa acccttttagg     960 gaaataggcc aggttttcac cgtaacacgc cacatcttgc gaatatatgt gtagaaactg      1020
ccggaaatcg tcgtggtatt cactccagag cgatgaaaac gtttcagttt gctcatggaa      1080
aacggtgtaa caagggtgaa cactatccca tatcaccagc tcaccgtctt tcattgccat      1140
acggaattcc ggatgagcat tcatcaggcg gcaagaatg tgaataaagg ccggataaaa       1200
cttgtgctta ttttctttta cggtctttaa aaaggccgta atatccagct gaacggtctg      1260
gttataggta cattgagcaa ctgactgaaa tgcctcaaaa tgttctttac gatgccattg      1320
ggatatatca acggtggtat atccagtgat ttttttctcc attttagctt ccttagctcc      1380
tgaaaatctc gataactcaa aaaatacgcc cggtagtgat cttatttcat tatggtgaaa      1440
gttggaacct cttacgtgcc gatcaacgtc tcatttttcgc caaaagttgg cccagggctt     1500
cccggtatca cagggacac caggatttat ttattctgcg aagtgatctt ccgtcacagg       1560
tatttattcg gcgcaaagtg cgtcgggtga tgcataactt cgtatagcat acattatacg      1620
aacggtaccc atcagatcca ctagcttgca ttgaacttgt ggataaaatc acggtccgat      1680
aaaacaatga atgataacct cgttgctctt aagctctggc acagttgttg ctaccactga      1740
agcgccagaa gatatcgatt gagaggattt gaatgactga caaaatgcaa agtttagctt      1800
tagccccagt tggcaacctg gattcctaca tccgggcagc taacgcgtgg ccgatgttgt      1860
cggctgacga ggagcgggcg ctggctgaaa agctgcatta ccatggcgat ctggaagcag      1920
ctaaaacgct gatccagtct cacctgcggt ttgttgttca tattgctcgt aattatgcgg      1980
gctatggcct gccacaggcg gatttgattc aggaaggtaa catcggcctg atgaaagcag      2040
tgcgccgttt caacccggaa gcgggtgtgc gcctggtctc cttcgccgtt cactggatca      2100
aagcagagat ccacgaatac gttctgcgta actggcgtat cgtcaaagtt gcgaccacca      2160
aagcgcagcg caaactgttc ttcaacctgc gtaaaaccaa gcagcgtctg ggctggttta      2220
accaggatga agtcgaaatg gtggcccgtg aactgggcgt aaccagcaaa gaagtacgtg      2280
agatggaatc acgtatggcg gcacaggaca tgaccttga cctgtcttcc gacgacgatt       2340
ccgacagcca gccgatggct ccggtgctct atctgcagga taaatcatct aactttgccg      2400
acggcattga agatgatatc tgggaagagc aggcggcaaa ccgtctgacc gacgcgatgc      2460
agggtctgga cgaacgcagc caggacatca tccgtgcgcg ctggctggac gaagacaaca      2520
agtccacgtt gcaggaactg gctgaccgtt acggcgtttc cgctgagcgt gtccgccagc      2580
tggaaaagaa cgcgatgaaa aaattgcgtg ctgccattga agcgtaattt ccgctattaa      2640
gcagagaacc ctggatgaga gtccggggtt tttgtttttt gggcctctgt aataatcaat      2700
ttcccctccg gcaaaacgcc aatccccacg cagattgtta ataaactgtc aaaatagcta      2760
ttccaatatc ataaaaatcg ggtatgtttt agcagagtat gctgctaaag cacgggtagt      2820
```

| catgcataaa acgaaataaa gtgctgaaaa acaacatcac aacacacgta ataaccagaa | 2880 |
| gaatggggat tctcaggatg aacataaagg gtaaagcgtt actggcagga tgtatcgcgc | 2940 |
| tggcattcag caatatggct ctggcagaag atattaaagt cgcggtcgtg ggcgcaatgt | 3000 |
| ccggtccggt tgcgcagtac ggtgaccagg agtttaccgg cgcagagcag gcggttgcgg | 3060 |
| atatcaacgc taaaggcggc attaaaggca acaaactgca aatcgtaaaa tatgacgatg | 3120 |
| cctgtgaccc gaaaca | 3136 |

<210> SEQ ID NO 14
<211> LENGTH: 984
<212> TYPE: DNA
<213> ORGANISM: Escherichia coli

<400> SEQUENCE: 14

| gcttgcattg aacttgtgga taaaatcacg gtctgataaa acagtgaatg ataacctcgt | 60 |
| tgctcttaag ctctggcaca gttgttgcta ccactgaagc gccagaagat atcgattgag | 120 |
| aggatttgaa tgactgacaa aatgcaaagt ttagctttag ccccagttgg caacctggat | 180 |
| tcctacatcc gggcagctaa cgcgtggccg atgttgtcgg ctgacgagga gcgggcgctg | 240 |
| gctgaaaagc tgcattacca tggcgatctg gaagcagcta aaacgctgat cctgtctcac | 300 |
| ctgcggtttg ttgttcatat tgctcgtaat tatgcgggct atggcctgcc acaggcggat | 360 |
| ttgattcagg aaggtaacat cggcctgatg aaagcagtgc gccgtttcaa cccggaagtg | 420 |
| ggtgtgcgcc tggtctcctt cgccgttcac tggatcaaag cagagatcca cgaatacgtt | 480 |
| ctgcgtaact ggcgtatcgt caaagttgcg accaccaaag cgcagcgcaa actgttcttc | 540 |
| aacctgcgta aaccaagca gcgtctgggc tggtttaacc aggatgaagt cgaaatggtg | 600 |
| gcccgtgaac tgggcgtaac cagcaaagac gtacgtgaga tggaatcacg tatggcggca | 660 |
| caggacatga cctttgacct gtcttccgac gacgattccg acagccagcc gatggctccg | 720 |
| gtgctctatc tgcaggataa atcatctaac tttgccgacg gcattgaaga tgataactgg | 780 |
| gaagagcagg cggcaaaccg tctgaccgac gcgatgcagg gtctggacga acgcagccag | 840 |
| gacatcatcc gtgcgcgctg gctggacgaa acaacaagt ccacgttgca ggaactggct | 900 |
| gaccgttacg gcgtttccgc tgagcgtgta cgccagctgg aaaagaacgc gatgaaaaaa | 960 |
| ttgcgtgctg ccattgaagc gtaa | 984 |

<210> SEQ ID NO 15
<211> LENGTH: 984
<212> TYPE: DNA
<213> ORGANISM: Escherichia coli

<400> SEQUENCE: 15

| gcttgcattg aacttgtgga taaaatcacg gtccgataaa acaatgaatg ataacctcgt | 60 |
| tgctcttaag ctctggcaca gttgttgcta ccactgaagc gccagaagat atcgattgag | 120 |
| aggatttgaa tgactgacaa aatgcaaagt ttagctttag ccccagttgg caacctggat | 180 |
| tcctacatcc gggcagctaa cgcgtggccg atgttgtcgg ctgacgagga gcgggcgctg | 240 |
| gctgaaaagc tgcattacca tggcgatctg gaagcagcta aaacgctgat ccagtctcac | 300 |
| ctgcggtttg ttgttcatat tgctcgtaat tatgcgggct atggcctgcc acaggcggat | 360 |
| ttgattcagg aaggtaacat cggcctgatg aaagcagtgc gccgtttcaa cccggaagcg | 420 |
| ggtgtgcgcc tggtctcctt cgccgttcac tggatcaaag cagagatcca cgaatacgtt | 480 |

```
ctgcgtaact ggcgtatcgt caaagttgcg accaccaaag cgcagcgcaa actgttcttc    540
aacctgcgta aaccaagca gcgtctgggc tggtttaacc aggatgaagt cgaaatggtg    600
gcccgtgaac tgggcgtaac cagcaaagaa gtacgtgaga tggaatcacg tatggcggca    660
caggacatga cctttgacct gtcttccgac gacgattccg acagccagcc gatggctccg    720
gtgctctatc tgcaggataa atcatctaac tttgccgacg gcattgaaga tgatatctgg    780
gaagagcagg cggcaaaccg tctgaccgac gcgatgcagg gtctggacga acgcagccag    840
gacatcatcc gtgcgcgctg gctggacgaa gacaacaagt ccacgttgca ggaactggct    900
gaccgttacg gcgtttccgc tgagcgtgtc cgccagctgg aaaagaacgc gatgaaaaaa    960
ttgcgtgctg ccattgaagc gtaa                                          984
```

<210> SEQ ID NO 16
<211> LENGTH: 284
<212> TYPE: PRT
<213> ORGANISM: Escherichia coli

<400> SEQUENCE: 16

```
Met Thr Asp Lys Met Gln Ser Leu Ala Leu Ala Pro Val Gly Asn Leu
1               5                   10                  15

Asp Ser Tyr Ile Arg Ala Ala Asn Ala Trp Pro Met Leu Ser Ala Asp
            20                  25                  30

Glu Glu Arg Ala Leu Ala Glu Lys Leu His Tyr His Gly Asp Leu Glu
        35                  40                  45

Ala Ala Lys Thr Leu Ile Leu Ser His Leu Arg Phe Val Val His Ile
    50                  55                  60

Ala Arg Asn Tyr Ala Gly Tyr Gly Leu Pro Gln Ala Asp Leu Ile Gln
65                  70                  75                  80

Glu Gly Asn Ile Gly Leu Met Lys Ala Val Arg Arg Phe Asn Pro Glu
                85                  90                  95

Val Gly Val Arg Leu Val Ser Phe Ala Val His Trp Ile Lys Ala Glu
            100                 105                 110

Ile His Glu Tyr Val Leu Arg Asn Trp Arg Ile Val Lys Val Ala Thr
        115                 120                 125

Thr Lys Ala Gln Arg Lys Leu Phe Phe Asn Leu Arg Lys Thr Lys Gln
    130                 135                 140

Arg Leu Gly Trp Phe Asn Gln Asp Glu Val Glu Met Val Ala Arg Glu
145                 150                 155                 160

Leu Gly Val Thr Ser Lys Asp Val Arg Glu Met Glu Ser Arg Met Ala
                165                 170                 175

Ala Gln Asp Met Thr Phe Asp Leu Ser Ser Asp Asp Ser Asp Ser
            180                 185                 190

Gln Pro Met Ala Pro Val Leu Tyr Leu Gln Asp Lys Ser Ser Asn Phe
        195                 200                 205

Ala Asp Gly Ile Glu Asp Asp Asn Trp Glu Glu Gln Ala Ala Asn Arg
    210                 215                 220

Leu Thr Asp Ala Met Gln Gly Leu Asp Glu Arg Ser Gln Asp Ile Ile
225                 230                 235                 240

Arg Ala Arg Trp Leu Asp Glu Asp Asn Lys Ser Thr Leu Gln Glu Leu
                245                 250                 255

Ala Asp Arg Tyr Gly Val Ser Ala Glu Arg Val Arg Gln Leu Glu Lys
            260                 265                 270

Asn Ala Met Lys Lys Leu Arg Ala Ala Ile Glu Ala
        275                 280
```

<210> SEQ ID NO 17
<211> LENGTH: 284
<212> TYPE: PRT
<213> ORGANISM: Escherichia coli

<400> SEQUENCE: 17

```
Met Thr Asp Lys Met Gln Ser Leu Ala Leu Ala Pro Val Gly Asn Leu
1               5                   10                  15

Asp Ser Tyr Ile Arg Ala Ala Asn Ala Trp Pro Met Leu Ser Ala Asp
            20                  25                  30

Glu Glu Arg Ala Leu Ala Glu Lys Leu His Tyr His Gly Asp Leu Glu
        35                  40                  45

Ala Ala Lys Thr Leu Ile Gln Ser His Leu Arg Phe Val Val His Ile
    50                  55                  60

Ala Arg Asn Tyr Ala Gly Tyr Gly Leu Pro Gln Ala Asp Leu Ile Gln
65                  70                  75                  80

Glu Gly Asn Ile Gly Leu Met Lys Ala Val Arg Arg Phe Asn Pro Glu
                85                  90                  95

Ala Gly Val Arg Leu Val Ser Phe Ala Val His Trp Ile Lys Ala Glu
            100                 105                 110

Ile His Glu Tyr Val Leu Arg Asn Trp Arg Ile Val Lys Val Ala Thr
        115                 120                 125

Thr Lys Ala Gln Arg Lys Leu Phe Phe Asn Leu Arg Lys Thr Lys Gln
    130                 135                 140

Arg Leu Gly Trp Phe Asn Gln Asp Glu Val Glu Met Val Ala Arg Glu
145                 150                 155                 160

Leu Gly Val Thr Ser Lys Glu Val Arg Glu Met Glu Ser Arg Met Ala
                165                 170                 175

Ala Gln Asp Met Thr Phe Asp Leu Ser Ser Asp Asp Ser Asp Ser
            180                 185                 190

Gln Pro Met Ala Pro Val Leu Tyr Leu Gln Asp Lys Ser Ser Asn Phe
        195                 200                 205

Ala Asp Gly Ile Glu Asp Asp Ile Trp Glu Glu Gln Ala Ala Asn Arg
    210                 215                 220

Leu Thr Asp Ala Met Gln Gly Leu Asp Glu Arg Ser Gln Asp Ile Ile
225                 230                 235                 240

Arg Ala Arg Trp Leu Asp Glu Asp Asn Lys Ser Thr Leu Gln Glu Leu
                245                 250                 255

Ala Asp Arg Tyr Gly Val Ser Ala Glu Arg Val Arg Gln Leu Glu Lys
            260                 265                 270

Asn Ala Met Lys Lys Leu Arg Ala Ala Ile Glu Ala
        275                 280
```

L-THREONINE-PRODUCING MICROORGANISM AND PRODUCTION METHOD FOR L-THREONINE USING THE SAME

CROSS REFERENCE TO RELATED APPLICATIONS

This application is a National Stage Entry of International Application No. PCT/KR2014/003613 filed on Apr. 24, 2014, and claims the benefit of Korean Application No. 10-2013-0072181, filed on Jun. 24, 2013, which is hereby incorporated by reference in its entirety for all purposes as if fully set forth herein

TECHNICAL FIELD

The present application relates to an RNA polymerase sigma-32 factor variant and a method of producing L-threonine using the same.

Incorporated by reference herein in its entirety is the Sequence Listing entitled "Sequence list.txt", created Dec. 18, 2015, size of 15 kilobytes.

BACKROUND ART

L-threonine, a kind of essential amino acid, is widely used as an additive to animal feed and food, and is also effectively used as rehydration solutions and synthetic materials for medical and pharmaceutical use. L-threonine is mainly produced by fermentation using *Escherichia coli* or *Corynebacterium*, developed by artificial mutation methods or gene recombination methods. Artificial mutant strains derived from wild-type strains, including *Escherichia coli, Serratia, Providencia* or *Corynebacterium*, are widely used for the production of L-threonine.

With the development of gene recombination technology, manipulation technologies for strains havingL-threonine productivity by random mutation, have been reported as site-specific gene replacement, gene amplification and deletion, etc. for the improved L-threonine productivity. Genes related to the biosynthesis of threonine and various methods for increasing the expression of these genes have been developed, but the demand for a method capable of producing L-threonine in higher yield still exists.

Global transcription machinery functions to control transcripts in all cellular systems (prokaryotic and eukaryotic). Global transcription machinery engineering provides recombinant cells comprising a global regulator having improved characters by mutating either a nucleic acid encoding the global regulator or a promoter controlling the expression thereof, and cells having improved phenotypes can be produced by this method.

A sigma factor is a type of global regulator that plays an important role in regulating global transcription based on the promoter preference of RNA polymerase holoenzyme. A sigma factor is a prokaryotic transcription initiation factor that enables specific binding of RNA polymerase to gene promoters. Each sigma factor is activated in response to different environmental condition, and every molecule of RNA polymerase contains one sigma factor subunit. It is known that *E. coli* has at least eight sigma factors and that the number of sigma factors varies depending on bacterial species.

The present inventors have conducted studies to modify the rpoH gene encoding sigma-32 known to control the heat shock response for the purpose of further enhancing the high-temperature stress resistance of an *E. coli* strain having L-threonine productivity. As a result, the present inventors have developed an RNA polymerase sigma-32 factor variant that regulates the transcriptional mechanism so that the threonine productivity does not greatly decrease even at high temperatures, and have introduced the RNA polymerase sigma-32 factor variant into a threonine-producing strain, thereby completing the present application.

DISCLOSURE

Technical Problem

It is an object of the present application to provide an RNA polymerase sigma-32 factor variant.

Another object of the present application is to provide a nucleotide sequence encoding the RNA polymerase sigma-32 factor variant.

Still another object of the present application is to provide a vector comprising the nucleotide sequence.

Still another object of the present application is to provide a recombinant microorganism of the genus *Escherichia* having L-threonine productivity, which expresses the variant.

Still another object of the present application is to provide a method of producing L-threonine using the microorganism of the genus *Escherichia*.

Technical Solution

In order to accomplish the above objects, the present application provides an RNA polymerase sigma-32 factor variant having an amino acid sequence represented by SEQ ID NO: 17.

The present application also provides a nucleotide sequence encoding the RNA polymerase sigma-32 factor variant.

The present application also provides a recombinant microorganism of the genus *Escherichia* having L-threonine productivity, which expresses the variant.

The present application also provides a method of producing L-threonine using the microorganism of the genus *Escherichia*.

Advantageous Effects

According to the present application, a strain transformed with a vector comprising a nucleotide sequence encoding an RNA polymerase sigma-32 factor variant having resistance to high-temperature stress has temperature resistance and can also produce L-threonine in increased yield. Thus, it can produce threonine with significantly high productivity compared to conventional strains, even when it is cultured at high temperatures. Accordingly, it can be effectively used to produce threonine in high yield.

Mode For Invention

Hereinafter, the present application will be described in detail.

The present application provides an RNA polymerase sigma-32 factor variant having an amino acid sequence represented by SEQ ID NO: 17.

As used herein, the term "sigma-32 ($\sigma^{32}$) factor" refers to the global regulator sigma factor known as a major sigma factor that controls the heat shock response in the log phase and that is encoded by the rpoH gene.

In addition, variants having a homology of at least 80%, specifically at least 90%, more specifically at least 95%, and particularly specifically at least 99%, to the amino acid sequences of the variant of the present application, are also included in the scope of the present application. The homology of the amino acid sequence can be determined by using, for example, the algorithm BLAST of Karlin and Altschul (see Pro. Natl. Acad. Sci. USA, 90, 5873 (1993)) or FASTA (see Methods Enzymol., 183, 63 (1990)). Programs called BLASTN and BLASTX have been developed on the basis of this algorithm BLAST (refer to www.ncbi.nlm.nih.gov). The scope of the variant of the present application includes mutants having a deletion, insertion, amino acid substitution and the like compared to the amino acid sequence of the variant, and also includes mutants having a codon substitution.

In an embodiment of the present application, a variant was selected from a mutated rpoH DNA pool obtained by introducing random mutations into the wild-type *E. coli* strain W3110, and the selected variant was named rpoH$^{2-G6}$. The nucleotide sequence of the extracted variant was analyzed, and as a result, it could be seen that a mutation in the amino acid sequence of the variant compared to the amino acid sequence (SEQ ID NO: 16) of a wild-type RNA polymerase sigma-32 factor occurred (Example 3).

The present application also provides a nucleotide sequence encoding the variant.

In an embodiment of the present application, the RNA polymerase sigma-32 factor variant may specifically have a nucleotide sequence represented by SEQ ID NO: 15.

In an embodiment of the present application, the genetic code of the nucleotide sequence encoding the variant may be degenerated. Herein, genetic code degeneracy is a phenomenon in which the very last letter in the genetic code is meaningless. If the first two bases are the same, they code the same, even when the codes in the positions are different.

Accordingly, the nucleotide sequence of the variant according to the present application may have a homology of at least 80%, specifically at least 90%, more specifically at least 95%, most specifically 99%, to a nucleotide sequence represented by SEQ ID NO: 15.

The present application also provides a vector comprising the nucleotide sequence.

The vector used in the present application is not specifically limited and may be any vector known in the art, as long as it can replicate in a host. Examples of the vectors that are commonly used include natural or recombinant plasmids, cosmids, viruses, and bacteriophages. For example, the phage vector or cosmid vector used in the present application may be pWE15, M13, λMBL3, λMBL4, λIXII, λASHII, λAPII, λt10, λtll, Charon4A, Charon2 1A or the like, and the plasmid vector used in the present application may be pBR type, pUC type, pBluescriptll type, pGEM type, pTZ type, pCL type, pET type or the like. A vector that may be used in the present application is not specifically limited and may be any expression vector known in the art. Specifically, a pACYC177, pACYC184, pCL, pECCG117, pUC19, pBR322, pMW118 or pCC1BAC vector may be used. Most specifically, a pACYC177, pCL or pCC1BAC vector may be used.

The present application provides a recombinant microorganism of the genus *Escherichia* having L-threonine productivity, which expresses the variant.

In the present application, expression of the variant can be achieved either by transformation with a recombinant vector operably comprising a gene encoding the variant or by insertion of a polynucleotide encoding the variant into the chromosome of the microorganism, but is not specifically limited thereto.

As used herein, the term "transformation" means introducing a vector comprising a polynucleotide encoding a target protein into a host cell so as to be able to express a protein encoded by the polynucleotide in the host cell. The introduced polynucleotide may be inserted and located in the chromosome of the host cell or located outside the chromosome, as long as it can be expressed in the host cell. In addition, the polynucleotides include DNA and RNA, which encode the target protein. As long as the polynucleotide can be introduced in the host cell and expressed therein, it may be introduced in any form. For example, the polynucleotide can be introduced into the host cell in the form of an expression cassette which is a polynucleotide construct including all elements required for self-expression. The expression cassette generally includes a promoter which is operably linked to the open reading frame (hereinafter abbreviated as "ORF") of the gene, a transcription termination signal, a ribosome binding site, and a translation termination signal. The expression cassette may be in the form of a self-replicable expression vector. In addition, the polynucleotide may be introduced into the host cell by itself and operably linked to the sequence necessary for expression in the host cell.

In the present application, transformation may be achieved either by transduction of a vector comprising a nucleotide sequence encoding the RNA polymerase sigma-32 factor variant or by insertion of the nucleotide sequence into the chromosome of the microorganism, but is not specifically limited thereto.

The microorganism of the present application includes any prokaryotic microorganism, as long as it can produce L-threonine. For example, it may include a microorganism belonging to the genus *Escherichia*, the genus *Erwinia*, the genus *Serratia*, the genus *Providencia*, the genus *Corynebacterium* or the genus *Brevibacterium*. Specifically, the microorganism used in the present application is the genus *Escherichia*. More specifically, it is *Escherichia coli*.

In an embodiment of the present application, a threonine-producing strain may be used as a parent strain. The threonine-producing strain may be an *E. coli* strain that has a methionine auxotroph phenotype, resistance to a threonine analogue, resistance to a lysine analogue, resistance to an isoleucine analogue, and resistance to a methionine analogue.

In addition, the threonine-producing strain may be a recombinant *E. coli* strain obtained by manipulating the threonine biosynthesis gene or the like. For example, it may be a recombinant *E. coli* strain having introduced therein one copy of each of phosphoenol pyruvate carboxylase (ppc) gene and an operon comprising aspartokinase L-homoserine dehydrogenase (thrA), homoserine kinase (thrB) and threonine synthase (thrC). Alternatively, it may be a recombinant *E. coli* strain obtained by inactivating both an operon gene (tdcBC), which is involved in L-threonine degradation, and phosphoenol pyruvate carboxykinase (pckA).

Specifically, a strain used in the present application may be a strain selected from the group consisting of *E. coli* KCCM10541P (Korean Patent No. 10-0576342), *E. coli* ABA5G/pAcscBAR'-M, pC-Ptrc-scrAB (Korean Patent No. 10-1145943) and *E. coli* KCCM11167P (Korean Patent Laid-Open Publication No. 10-2012-0083795).

In an embodiment of the present application, the transformed microorganism may be *E. coli* FTR2700.

In an embodiment of the present application, the microorganism of the present application may be an *E. coli* strain having one or more desired phenotypes for enhancing L-threonine productivity. Specifically, the one or more desired phenotypes are temperature-resistant phenotypes.

The present application also provides a method of producing L-threonine using the transformed strain.

The culture method in the present application can be performed in suitable media and culture conditions known in the art. This culture method can be easily modified by any person skilled in the art depending on the type of strain selected. Examples of the culture method include, but are not limited to, batch culture, continuous culture, and fed-batch culture.

The medium and culture conditions that are used in culture of the microorganism of the present application may be any of those that are generally used in culture of microorganisms of the genus *Escherichia*, but these should properly satisfy the requirements of the microorganism of the present application.

In a specific embodiment, the microorganism of the present application may be cultured in a conventional medium containing suitable carbon sources, nitrogen sources, amino acids, vitamins and the like under aerobic conditions while adjusting temperature, pH and the like.

Carbon sources that may be used in the present application include carbohydrates such as glucose, fructose, sucrose, maltose, mannitol, sorbitol; alcohols such as sugar alcohol, glycerol, pyruvic acid, lactic acid and citric acid; and amino acids such as organic acid, glutamic acid, methionine and lysine. In addition, natural organic nutrient sources such as starch hydrolysates, molasses, blackstrap molasses, rice bran, cassava, bagasse and corn steep liquor may be used. Specifically, carbohydrates such as glucose and sterile pretreated molasses (i.e., molasses converted to reduced sugars) may be used. In addition, suitable amounts of other carbon sources may be used without limitation. Nitrogen sources that may be used in the present application include inorganic nitrogen sources such as ammonia, ammonium sulfate, ammonium chloride, ammonium acetate, ammonium carbonate, and ammonium nitrate; amino acids such as glutamic acid, methionine and glutamine; and organic nitrogen sources such as peptone, NZ-amine, meat extract, yeast extract, malt extract, corn steep liquor, casein hydrolysate, fish meal or its digested product, defatted soybean cake or its digested product, etc. These nitrogen sources may be used alone or in combination. The medium may contain, as phosphorus sources, potassium phosphate monobasic, potassium phosphate dibasic and corresponding sodium-containing salts. Inorganic compounds that may be used in the present application include sodium chloride, calcium chloride, iron chloride, magnesium sulfate, iron sulfate, manganese sulfate and calcium carbonate. In addition, the medium may contain amino acids, vitamins and suitable precursors. These sources or precursors may be added to the medium in a batch or continuous manner.

Compounds such as ammonium hydroxide, potassium hydroxide, ammonia, phosphoric acid and sulfuric acid may be added to the medium in a suitable manner during culture to adjust the pH of the culture medium. In addition, during the culture, an antifoaming agent such as fatty acid polyglycol ester may be used to suppress the formation of bubbles. Further, in order to maintain the culture medium in an aerobic state, oxygen or oxygen-containing gas may be injected into the culture medium. In addition, in order to maintain the culture medium in an anaerobic or non-aerobic state, no gas is injected, or nitrogen, hydrogen or carbon dioxide gas may be injected into the culture medium. The culture medium may be typically maintained at a temperature ranging from 27° C. to 37° C., and specifically from 30° C. to 37° C. Culture of the microorganism may be continued until the desired level of the useful substance will be obtained. Specifically, the culture period may be 10-100 hours.

The method of the present application may further comprise a step of purifying or recovering the L-threonine produced in the culture step. The purification or recovery method may be performed by purifying or recovering the desired L-threonine from the culture medium using a suitable method depending on a method used for culture of the microorganism in the present application, for example, a batch, continuous or fed-batch culture method.

Hereinafter, the present application will be described in further detail with reference to examples. It is to be understood, however, that these examples are for illustrative purposes only and are not intended to limit the scope of the present application.

EXAMPLES

Example 1

Construction of Recombinant Vector pCC1BAC-rpoH (1) Preparation of rpoH Gene Fragment In order to obtain an about 1.0 kb DNA fragment comprising the rpoH gene (nucleotide sequence of SEQ ID NO: 14 and amino acid sequence of SEQ ID NO: 16), the genomic DNA (gDNA) of the wild-type *E. coli* strain W3110 was isolated with a Genomic-tip system (Qiagen). Using the gDNA as a template, polymerase chain reaction (hereinafter abbreviated as "PCR") was performed using a PCR HL premix kit (BIONEER, hereinafter the same).

The PCR reaction for amplifying the rpoH gene was performed using primers of SEQ ID NOS: 1 and 2 for 27 cycles, each consisting of denaturation at 94° C. for 30 sec, annealing at 55° C. for 30 sec and elongation at 72° C. for 1 min.

The PCR product was digested with EcoRI, and the 1.0-kb DNA fragment (hereinafter referred to as "rpoH fragment") was electrophoresed on 0.8% agarose gel, and then collected by elution.

(2) Construction of Recombinant Vector pCC1BAC-rpoH

A copycontrol pCC1BAC EcoRI cloning-ready vector (EPICENTRE (USA)) and the rpoH obtained in Example 1-(1) were each treated with the restriction enzyme EcoRI and were ligated with each other, thereby constructing a pCC1BAC-rpoH plasmid.

Example 2

Library Construction of Recombinant Vector pCC1BAC-rpoH Variants (1) Preparation of rpoH Variants by Error-Prone PCR In order to obtain a DNA pool consisting of rpoH variant fragments having random mutations introduced therein, PCR was performed using the W3110 gDNA (extracted in Example 1-(1)) as a template under the conditions of mutagenesis reactions 4 shown in Table III of the user manual of a diversify PCR random mutagenesis kit (catalog No. K1830-1; Clonetech). The PCR was performed using primers of SEQ ID NOS: 1 and 2 for 25 cycles, each consisting of denaturation at 94° C. for 30 sec and elongation at 68° C. for 1 min.

The PCR product was digested with EcoRI, and the 1.0-kb DNA fragment (hereinafter referred to as "rpoH'" fragment") was electrophoresed on 0.8% agarose gel, and then collected by elution.

(2) Library Construction of Recombinant Vector pCC1BAC-rpoH Variants

A copycontrol pCC1BAC EcoRI cloning-ready vector was ligated with the rpoH'" fragment obtained in Example 2-(1), thereby constructing a pCC1BAC-rpoH'" vector.

The constructed vector was transformed into Transfor-Max EPI300 Electrocompetent *E. coli* (EPICENTRE), and then colony selection on LB plate+15 μg/ml chloramphenicol+40 μg/ml X-Gal+0.4mM IPTG was performed. It was confirmed that no blue colony was detected. The selected colonies were collected and subjected to plasmid prep, thereby constructing a library of pCC1BAC-rpoH variants.

(3) Introduction of pCC1BAC-rpoH Variants into Threonine-Producing Strain

Each of pCC1BAC-rpoH, obtained in Example 1-(2), and the pCC1BAC-rpoH variant library obtained in Example 2-(2), was introduced by transformation into the threonine-producing *E. coli* strain KCCM 10541 prepared in a competent manner, and the resulting strains were named "KCCM 10541/pCC1BAC-rpoH" and "KCCM 10541/pCC1BAC-rpoH mutant library", respectively.

The *E. coli* strain KCCM10541 used as the parent strain in this Example is a strain having enhanced L-threonine productivity as a result of inactivating the tyrR gene and galR gene present in the chromosome of the parent strain *Escherichia coli* KCCM 10236 having characteristics, including a methionine auxotroph phenotype, a leaky isoleucine auxotroph phenotype, resistance to an L-threonine analogue (e.g., α-amino-β-hydroxy valeric acid (AHV)), resistance to an L-lysine analogue (e.g., S-(2-aminoethyl)-L-cysteine (AEC)), resistance to an isoleucine analogue (e.g., α-aminobutyric acid), and resistance to a methionine analogue (e.g., ethionine) (Korean registered Patent No. 10-0576342).

Example 3

Selection of RNA Polymerase Sigma-32 Factor Variant Having Resistance to Temperature In this Example, an experiment was performed to select an RNA polymerase sigma-32 factor variant having resistance to temperature.

Each of the *E. coli* KCCM 10541/pCC1BAC-rpoH and *E. coli* KCCM 10541/pCC1BAC-rpoH mutant library prepared in Example 2-(3) was cultured overnight on LB solid media in an incubator at 37° C. and 33° C. One platinum loop of each of the cultured strain was inoculated into 25 mL of the titer medium shown in Table 1 below, and then cultured in a shaking incubator at 37° C., 33° C. and 200 rpm for 48 hours.

TABLE 1

| Composition | Concentration (per liter) |
|---|---|
| Glucose | 70 g |
| KH$_2$PO$_4$ | 2 g |
| (NH$_4$)$_2$SO$_4$ | 27.5 g |
| MgSO$_4$•7H$_2$O | 1 g |

TABLE 1-continued

| Composition | Concentration (per liter) |
|---|---|
| FeSO$_4$•7H$_2$O | 5 mg |
| MnSO$_4$•4H$_2$O | 5 mg |
| DL-methionine | 0.15 g |
| Yeast extract | 2 g |
| Calcium carbonate | 30 g |
| pH | 6.8 |

Each of the colonies having the rpoH variant library introduced therein was cultured at 37° C., and variants showing an increase in the concentration of threonine compared to KCCM10541/pCC1BAC-rpoH were selected and cultured at 33° C. In this way, evaluation of the rpoH mutant library was performed by repeating the culture and selection method. Through this method, a clone improved in both temperature resistance and yield was selected. A vector was extracted from the selected clone and named pCC1BAC-rpoH$^{2-G6}$.

In order to detect a mutation in pCC1BAC-rpoH$^{2-G6}$, pCC1BAC-rpoH$^{2-G6}$ was amplified by PCR using primers of pIB FP (SEQ ID NO: 3) and pIB RP (SEQ ID NO: 4) provided as primers for detection in the copycontrol pCC1BAC EcoRI cloning-ready vector, and the PCR product was sequenced. The results of the sequencing indicated that rpoH$^{2-G6}$ (SEQ ID NO: 15), an rpoH variant, had an amino acid sequence of SEQ ID NO: 17.

Example 4

L-Threonine Productivity Comparison of Recombinant Strain

The vector pCC1BAC-rpoH$^{2-G6}$ obtained in Example 3 was transformed into *E. coli* KCCM 10541 to thereby prepare *E. coli* KCCM 10541/pCC1BAC-rpoH$^{2-G6}$.

Each of the parent strain *E. coli* KCCM 10541, the *E. coli* KCCM 10541/pCC1BAC-rpoH strain and the *E. coli* KCCM 10541/pCC1BAC-rpoH$^{2-G6}$ strain was cultured in an Erlenmeyer flask using the threonine titer medium shown in Table 1 above, and the L-threonine productivities thereof were analyzed. The results of the analysis are shown in Table 2 below.

TABLE 2

| | L-threonine (g/L) | |
|---|---|---|
| Strain | 33° C. | 37° C. |
| KCCM 10541 (parent strain) | 30.6 | 25.0 |
| KCCM 10541/pCC1BAC-rpoH | 30.5 | 26.1 |
| KCCM 10541/pCC1BAC-rpoH$^{2-G6}$ | 31.1 | 31.8 |

As shown in Table 2 above, the parent strain *E. coli* KCCM10541 and the control strain KCCM10541/pCC1BAC-rpoH produced 30.6 g/L and 30.5 g/L of L-threonine, respectively, when they were cultured for 48 hours, but the *E. coli* KCCM 10541/pCC1BAC-rpoH$^{2-G6}$ strain produced 31.1 g/L of L-threonine, and thus showed an increase in L-threonine productivity of about 1% P compared to the parent strain.

At 37° C., the parent strain (KCCM 10541) and the control strain (KCCM10541/pCC1BAC-rpoH) showed a decrease in the yield, whereas the KCCM 10541/pCC1BAC-rpoH$^{2-G6}$ strain showed no temperature-dependent decrease in the concentration of L-threonine productivity and produced 31.8 g/L of L-threonine, suggesting that it shows an increase in threonine productivity of about 8% P compared to the control group when it is cultured at high temperatures.

Example 5

Effects Comparison of Selected rpoH Variant (rpoH$^{2-G6}$) using other Threonine-Producing Strains (1) Effects Analysis of rpoH Variant (rpoH$^{2-G6}$) in ABA5G/pAcscBAR'-M, pC-Ptrc-scrAB Strain Effects of the vector pCC1BAC-rpoH$^{2-G6}$ confirmed in Example 4, the vector was introduced into the threonine-producing strain ABA5G/pAcscBAR'-M, pC-Ptrc-scrAB (Korean Patent No. 10-1145943) to thereby construct ABA5G/pAcscBAR'-M, pC-Ptrc-scrAB, pCC1BAC-rpoH$^{2-G6}$. Then titer evaluation was performed using the titer medium prepared as shown in Table 3 below. The results of the evaluation are shown in Table below.

The parent strain ABA5G/pAcscBAR'-M, pC-Ptrc-scrAB used in this Example is an E. coli strain having L-threonine productivity, obtained by transforming the threonine-producing strain ABA5G (which is a strain constructed by inducing an NTG mutation in the parent strain E. coli W3110 and having a methionine auxotroph phenotype, a leaky isoleucine auxotroph phenotype, resistance to α-amino-β-hydroxy valeric acid, resistance to 2-amino-ethyl)-L-cysteine, and resistance to 1-azetidine-2-carboxylic acid) with a vector comprising a pAcscBAR'-M gene group and a pC-Ptrc-scrAB gene group.

TABLE 3

| Composition | Concentration (per liter) |
| --- | --- |
| Sucrose | 70 g |
| KH$_2$PO$_4$ | 2 g |
| (NH$_4$)$_2$SO$_4$ | 27.5 g |
| MgSO$_4$•7H$_2$O | 1 g |
| FeSO$_4$•7H$_2$O | 5 mg |
| MnSO$_4$•4H$_2$O | 5 mg |
| DL-methionine | 0.15 g |
| Yeast extract | 2 g |
| Calcium carbonate | 30 g |
| pH | 6.8 |

TABLE

| | L-threonine (g/L) | |
| --- | --- | --- |
| Strain | 33° C. | 37° C. |
| ABA5G/pAcscBAR'-M, pC-Ptrc-scrAB | 22.8 | 19.8 |
| ABA5G/pAcscBAR'-M, pC-Ptrc-scrAB, pCC1BAC-rpoH$^{2-G6}$ | 22.8 | 22.0 |

As can be seen in Table 4 above, when the vector pCC1BAC-rpoH$^{2-G6}$ was introduced into threonine-producing strains other than E. coli KCCM10541, the threonine yield at 33° C. was maintained at a level similar to that shown in Table 2 above, and the threonine yield at 37° C. was maintained at a level similar to the threonine yield observed at 33° C.

(2) Effects Analysis of rpoH Variant (rpoH$^{2-G6}$) in E. coli KCCM11167P Strain The vector pCC1BAC-rpoH$^{2-G6}$ was introduced into another threonine-producing strain E. coli KCCM11167P (Korean Patent Application No. 2011-0005136) to thereby construct E. coli KCCM11167P/pCC1BAC-rpoH$^{2-G6}$, and the threonine productivity of the constructed strain was evaluated using the titer medium prepared as shown in Table 1 above. The results of the evaluation are shown in Table 5 below.

The parent strain E. coli KCCM11167P used in this Example is a strain obtained by inactivating tdcB in a KCCM10541 strain (Korean Patent No. 10-0576342) and enhancing nadK to two copies to enhance NAD kinase activity.

TABLE 5

| | L-threonine (g/L) | |
| --- | --- | --- |
| Strain | 33° C. | 37° C. |
| KCCM11167P | 30.1 | 26.2 |
| KCCM11167P/pCC1BAC-rpoH$^{2-G6}$ | 30.2 | 29.8 |

As can be seen in the titer evaluation results in Table 5 above, when pCC1BAC-rpoH$^{2-G6}$ was introduced into the strain having threonine productivity, the threonine yield at 33° C. was maintained and the threonine yield at 37° C. was maintained at a level similar to the threonine yield at 33° C., like when pCC1BAC-rpoH$^{2-G6}$ was introduced into the different threonine-producing strain as described in Example 5-(1).

Example 6

Additional Insertion of Selected rpoH Variant (rpoH$^{2-G6}$) into Chromosomes (1) Preparation of the rpoH$^{2-G6}$ Integration Cassette Fragment In order to additionally insert the rpoH$^{2-G6}$ variant, selected in Example 3, into a chromosome, a linear integration cassette was constructed. The linear integration cassette was constructed in the following manners.

PCR was performed using E. coli W3110 gDNA as a template and primers of SEQ ID NOS: 5 and 6. The PCR was performed for 27 cycles, each consisting of denaturation at 94° C. for 30 sec, annealing at 55° C. for 30 sec, and elongation at 72° C. for 30 sec. The resulting DNA fragment was named "homologous region 1".

Using pMloxCmt as a template and primers of SEQ ID NOS: 7 and 8, PCR for amplifying a mutant loxP-Cmr-loxP cassette was performed for 27 cycles, each consisting of denaturation at 94° C. for 30 sec, annealing at 55° C. for 30 sec, and elongation at 72° C. for 1 min. Herein, pMloxCmt used as the template is a vector constructed by a person skilled in the art based on a report of an improved gene deletion method that uses mutant loxP, named lox71 and lox66 by Suzuki et al. (Suzuki N. et al., Appl. Environ. Microbiol. 71:8472, 2005).

The obtained homologous region 1 and mutant loxP-Cm$^r$-loxP cassette fragment were subjected to overlap extension PCR using primers of SEQ ID NOS: 5 and 8, thereby obtaining "homologous region 1-mutant loxP-Cm$^r$-loxP". Herein, the PCR was performed in the absence of primers for 5 cycles, each consisting of denaturation at 94° C. for 30 sec, annealing at 55° C. for 30 sec, and elongation at 72° C. for 90 sec, and then performed in the presence of primers for 23 cycles.

Using pCC1BAC-rpoH$^{2\text{-}G6}$ as a template and primers of SEQ ID NOS: 9 and 10, PCR was performed for 27 cycles, each consisting of denaturation at 94° C. for 30 sec, annealing at 55° C. for 30 sec, and elongation at 72° C. for 1 min.

Using *E. coli* W3110 gDNA as a template and primers of SEQ ID NOS: 11 and 12, PCR was performed for 27 cycles, each consisting of denaturation at 94° C. for 30 sec, annealing at 55° C. for 30 sec, and elongation at 72° C. for 30 sec. The resulting DNA fragment was named "homologous region 2".

rpoH$^{2\text{-}G6}$ and homologous region 2 were subjected to overlap extension PCR using primers of SEQ ID NOS: 9 and 12, thereby obtaining "rpoH$^{2\text{-}G6}$-homologous region 2". Herein, the PCR was performed in the absence of primers for 5 cycles, each consisting of denaturation at 94° C. for 30 sec, annealing at 55° C. for 30 sec, and elongation at 72° C. for 90 sec, and then performed in the presence of primers for 23 cycles.

Using the obtained "homologous region 1-mutant loxP-Cm$^r$-loxP", "rpoH$^{2\text{-}G6}$-homologus region 2" as a template and primers of SEQ ID NOS: 5 and 12, overlap extension PCR was performed, thereby constructing an rpoH$^{2\text{-}G6}$ integration cassette. Herein, the PCR was performed in the absence of primers for 5 cycles, each consisting of denaturation at 94° C. for 30 sec, annealing at 55° C. for 30 sec, and elongation at 72° C. for 3 min, and then performed in the presence of primers for 23 cycles. As a result, an rpoH$^{2\text{-}G6}$ integration cassette represented by SEQ ID NO: 13 was constructed.

(2) Additional insertion of rpoH$^{2\text{-}G6}$ variant into chromosomes of Recombinant Strain In order to insert the selected rpoH$^{2\text{-}G6}$ variant into a chromosome, the rpoH$^{2\text{-}G6}$ integration cassette constructed in Example 6-(1) was purified, and the rpoH$^{2\text{-}G6}$ variant was additionally inserted into a chromosomal region following the already existing rpoH of *E. coli* KCCM10541 in the same manner as a known one-step inactivation method (Warner et al., PNAS, 6; 97(12):6640, 2000). Next, the antibiotic resistance marker gene was removed, thereby constructing a strain having the rpoH$^{2\text{-}G6}$ variant additionally inserted therein, and the construct was sequenced to ensure that no PCR error was introduced. The constructed strain having rpoH$^{2\text{-}G6}$ additionally inserted therein was named "FTR2700", and the transformed *E. coli* FTR2700 was deposited with the Korean Culture Center of Microorganisms (hereinafter abbreviated as KCCM) on Feb. 5, 2013 under the accession number KCCM11368P.

(3) L-Threonine Productivity Analysis

The recombinant microorganism constructed in Example 6-(2) was cultured in an Erlenmeyer flask using the threonine titer medium shown in Table 1 above, and the L-threonine productivity of the microorganism was analyzed.

One platinum loop of each of *E. coli* KCCM 10541 and *E. coli* KCCM11368P, cultured overnight on LB solid medium in an incubator at 33° C. and 37° C., was inoculated into 25 mL of the titer medium shown in Table 1 above, and then each of the *E. coli* strains was cultured in a shaking incubator at 33° C., 37° C. and 200 rpm for 48 hours.

As can be seen in Table 6 below, when the parent strain *E. coli* KCCM10541 was cultured for 48 hours, it produced 30.3 g/L of L-threonine, and the *E. coli* strain KCCM 11368P constructed in Example 6-(2) of the present application produced 30.0 g/L of L-threonine, and thus showed L-threonine productivity similar to that of the parent strain. The parent strain (KCCM 10541) showed a decrease in the L-threonine yield at 37° C., whereas the KCCM 11368P strain showed no temperature-dependent decrease in the L-threonine concentration and showed an increase in the L-threonine concentration.

Thus, it can be seen that, like the strain transformed with the vector, the strain constructed in Example 6-(2), when cultured at 37° C., shows threonine productivity similar to or higher than that obtained when it is cultured at 33° C.

TABLE 6

| Strain | L-threonine (g/L) | |
|---|---|---|
| | 33° C. | 37° C. |
| KCCM 10541 (parent strain) | 30.3 | 26.0 |
| KCCM 11368P | 30.0 | 32.0 |

While the present application has been described with reference to the particular illustrative embodiments, it will be understood by those skilled in the art to which the present application pertains that the present application may be embodied in other specific forms without departing from the technical spirit or essential characteristics of the present application. Therefore, the embodiments and experimental examples herein are considered to be illustrative in all respects and not restrictive. Furthermore, the scope of the present application is defined by the appended claims rather than the detailed description, and it should be understood that all modifications or variations derived from the meanings and scope of the present application and equivalents thereof are included in the scope of the appended claims.

Accession Number
Depository authority: Korean Culture Center of Microorganisms;
Accession number: KCCM11368P;
Deposit date: Feb. 5, 2013.

The invention claimed is:

1. An RNA polymerase sigma-32 factor variant having the amino acid sequence of SEQ ID NO: 17.

2. A recombinant microorganism of the genus *Escherichia* having L-threonine productivity, which expresses the variant of claim 1.

3. The recombinant microorganism of the genus *Escherichia* having L-threonine productivity according to claim 2, wherein the recombinant microorganism is transformed either by recombinant vector comprising a nucleotide sequence encoding an RNA polymerase sigma-32 factor variant having the amino acid sequence of SEQ ID NO: 17, or by additional insertion of the nucleotide sequence into a chromosome.

4. The recombinant microorganism of the genus *Escherichia* having L-threonine productivity according to claim 3, wherein the nucleotide sequence is SEQ ID NO: 15.

5. The recombinant microorganism of the genus *Escherichia* having L-threonine productivity according to claim 3, wherein the microorganism of the genus *Escherichia* is *Escherichia coli*.

6. A method for producing L-threonine, comprising the steps of:

culturing a recombinant microorganism of the genus Escherichia having L-threonine productivity of claim 2, and recovering L-threonine from the microorganism or the culture.

7. A nucleotide sequence encoding the RNA polymerase sigma-32 factor variant of claim 1.

8. The nucleotide sequence according to claim 7, wherein the nucleotide sequence is SEQ ID NO: 15.

9. A vector comprising the nucleotide sequence of claim 7.

* * * * *